United States Patent [19]

Niskin

[11] 4,037,477
[45] July 26, 1977

[54] WATER SAMPLER DEVICE

[76] Inventor: Shale J. Niskin, 2941 Lucaya, Coconut Grove, Fla. 33133

[21] Appl. No.: 691,905

[22] Filed: June 1, 1976

[51] Int. Cl.² ............................................. G01N 1/10
[52] U.S. Cl. ................................. 73/425.4 R; 73/300
[58] Field of Search .......................... 73/425.4 R, 300; 33/126.4 R, 126.4 A; 251/315

[56] References Cited

U.S. PATENT DOCUMENTS

| | | | |
|---|---|---|---|
| 1,838,729 | 12/1931 | Andrews | 73/425.4 R |
| 2,314,372 | 3/1943 | Spilhaus | 73/425.4 R |
| 2,391,978 | 1/1946 | Kahl | 73/425.4 R |
| 3,161,053 | 12/1964 | Bell | 73/425.4 R |
| 3,563,265 | 2/1971 | Graham | 251/315 X |
| 3,576,309 | 4/1971 | Zawacki | 251/315 X |
| 3,841,156 | 10/1974 | Wolfe | 73/425.4 X |

FOREIGN PATENT DOCUMENTS

| | | | |
|---|---|---|---|
| 12,119 | 9/1907 | United Kingdom | 33/126.4 R |

*Primary Examiner*—Richard C. Queisser
*Assistant Examiner*—Daniel M. Yasich

[57] ABSTRACT

A water sampler device having a cylindrical container open at each end with a ball valve mounted at the openings adapted to rotate about their axis from an initially closed position when the device is launched into a body of water to prevent the contamination of the container by the surface waters. Upon descending, a water pressure operated valve opens to equalize the pressure inside the container with that of the outside water pressure and causes the simultaneous rotation of the valves to an open position to permit water to flush through the device until it reaches the predetermined depth at which the sample is to be obtained when the valves are rotated again to a closed position. As the sampler device is being brought up to the surface, a further pressure operated valve permits the bleeding of water from within the device to equalize the pressure within the device with that of the surrounding area.

11 Claims, 25 Drawing Figures

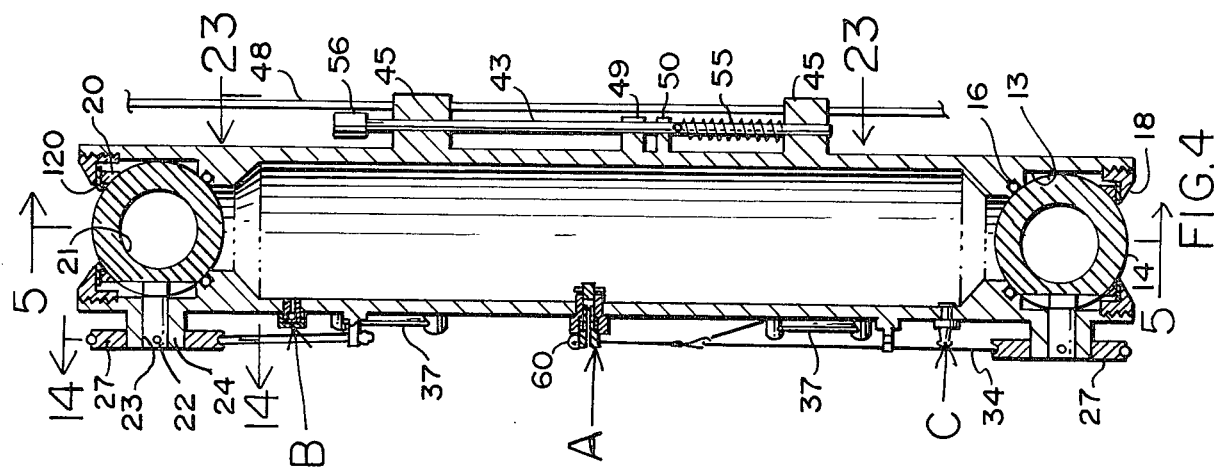
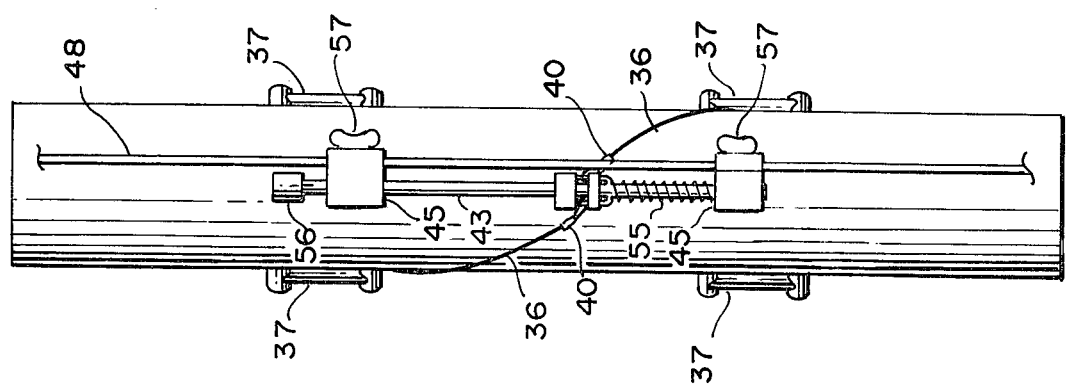
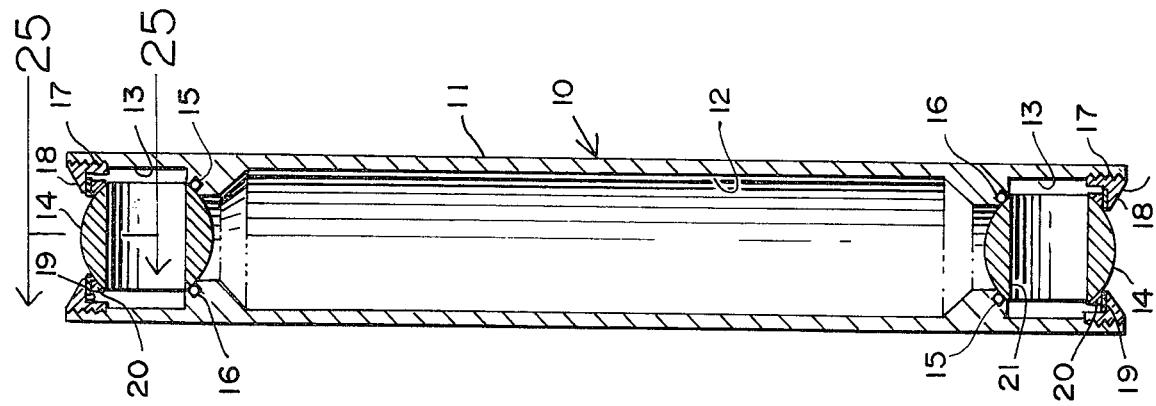
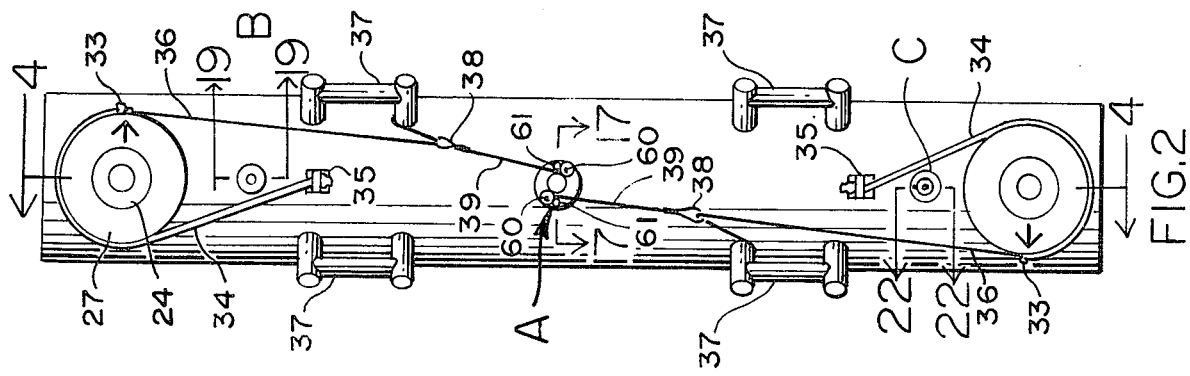

WATER SAMPLER DEVICE

BACKGROUND OF THE INVENTION

1. Field Of The Invention

This invention relates to water sample collecting devices and is more particularly directed to such a device having an open ended tubular member with a rotatable valve at each end for collecting and containing a sample of water taken from a predetermined depth in a body of water.

2. Description Of The Prior Art

As are indicated in my U.S. Pat. No. 3,242,740, entitled WATER SAMPLING SYSTEM, U.S. Pat. No. 3,815,422, entitled MULTI-CAPACITY WATER SAMPLER, and U.S. Pat. No. 3,489,012 entitled WATER SAMPLER DEVICE, the most effective conventional water sample collecting devices consist of a pliable container type as described in the first named patent and a rigid hollow container that is valved at both ends to entrap and contain a sample of water as described in my last named patent. The pliable container type is limited as to the quantity of water that can be obtained in each of the pliable containers. Consequently the hollow container having valves at each end is the more economical and effective type. However, difficulty was encountered in obtaining uncontaminated samples of water since the hollow containers are launched with the valves in an open position. Since the surface of a body of water is often badly contaminated, the insides of the bottles become immediately contaminated as they enter the body of water. Even though water is flushed through the containers as the devices descend to the depth at which the sample is to be obtained, the containers remain contaminated rendering the samples of water of little value. At the very best, the users of these devices are never assured that the sample of water thusly obtained is a true sample of the water at the depth it was collected. It is contemplated by the present invention to provide a water sampler device that avoids the above indicated objection by preventing the device from becoming contaminated upon immersion into the body of water of which the sample is to be obtained.

BRIEF SUMMARY OF THE INVENTION

Therefore a principal object of the present invention is to provide a water sampler device of the hollow rigid container type having values at each end that are in a closed position at the time the device is launched and remain closed for a relatively short period until the device has reached a desired depth.

Another object of the present invention is to provide an elongated water sampler device with rotatable ball valves mounted at each end for containing a sample of uncontaminated water within the device.

A further object of the present invention is to provide a water sampler device having a tubular member with ball valves mounted on each end in a normally closed position, which valves are rotated to an open position by a water pressure actuated device to permit water to flush through the tubular member until the latter has reached the depth at which the sample is to be taken.

A still further object of the present invention is to provide a water sampler device having ball valves with pressure equalizing valve means that permit the valves to rotate about their axes from an initially closed position to an open position and then to a closed position for containing a sample of water collected at a predetermined depth.

With these and other objects in view, the invention will be best understood from a consideration of the following detailed description taken in conjunction with the accompanying drawings forming a part of this specification, with the understanding, however, that the invention is not confined to any strict conformity with the showing of the drawings but may be changed or modified so long as such changes or modifications mark no material departure from the salient features of the invention as expressed in the appended claims.

BRIEF DESCRIPTION OF THE SEVERAL VIEWS OF THE DRAWINGS

In the drawings:

FIG. 2 is vertical front view of the device ready for launching with the ball valves in a closed position.

FIG. 3 is a similar view of the obverse side.

FIG. 4 is a cross sectional view taken along the line 4—4 of FIG. 2.

FIG. 5 is a similar view taken along the line 5—5 of FIG. 4.

DETAILED DESCRIPTION OF THE PREFERRED EMBODIMENT

Figure 25:
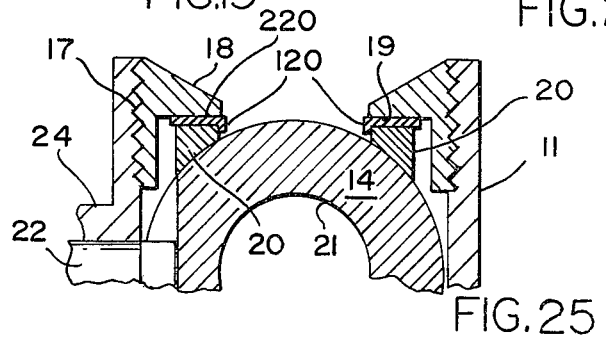
FIG. 25 is a fragmentary cross sectional view taken along the line 25—25 of FIG. 5.

Referring now to the drawings wherein like numerals are used to designate similar parts throughout the several views, the numeral 10 refers to my water sampler device consisting of an elongated tubular member or bottle 11 having a chamber 12 which is adapted to collect and retain a water sample therein. At each end of the bottle 11 is a valve chamber 13 constructed and arranged to retain a spherical or ball valve 14 therein. The valve chambers 13 which permit the rotation of the ball valves 14 are each provided with a peripheral groove 15 for retaining an O-ring 16 upon which the ball valves 14 seat and seal against the flow of water therethrough when in a closed position. The free ends of the bottle 11 are threaded as 17 for threadedly receiving a lock ring 18 having a peripheral shoulder 19 that engages a floating valve seat retainer ring 220. Positioned on the arcuate surface of the spherical valve 14 is a pliable valve seat ring 20 retained in and supported thereon by the floating valve seat retainer ring 220. See FIGS. 21 and 25. A lip portion 120 formed on the ring 220 engages the valve seat ring 20 to prevent the distortion of the pliable valve seat ring 20 as the ball valve 14 is rotated. In addition thereto, the floating valve seat ring 220 allows the ball valve 14 to seek the proper concentric alignment with the O-ring 16 in order to effect a perfect seal between the ball valve 14 and the O-ring 16. Note, that the outside diameter of the floating valve seat ring 220 is less than the outside diameter of the shoulder 19 forming a clearance therebetween to permit the sliding movement of the floating valve seat ring 220 as shown by FIG. 25.

Figure 12:
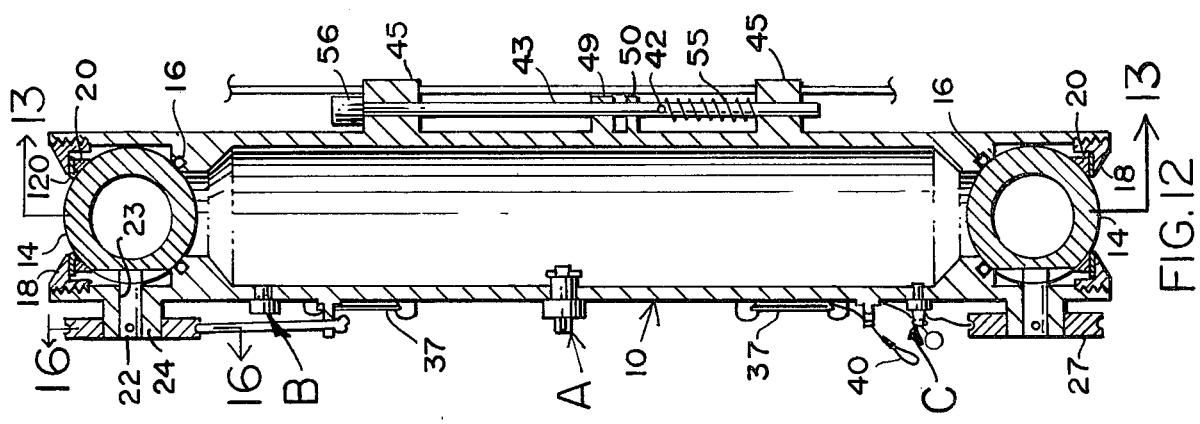
FIG. 12 is a cross sectional view taken along the line 12—12 of FIG. 10.

The ball valves 14 are of similar construction and operation and are each provided with an opening 21 that extends radially through the valve body for the flow of water into the bottle 11 when in an open position. Means for operating the ball valves 14 consist of a valve stem 22 rotatably mounted in an opening 23 formed in a boss 24 secured to the bottle 11. The inner end of the valve stem 22 is provided with a rectangular shaped finger portion 25 that is fitted into a similarly shaped slot 26 formed on the ball valve 14 whereby rotation of the stems 22 will cause a similar rotation of the ball valves 14. See FIGS. 8 and 12.

Figure 14:
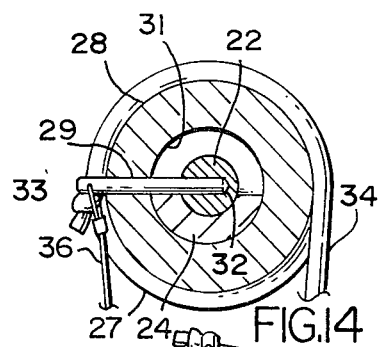
FIG. 14 is a detailed cross sectional view of the ball valve actuator pulley taken along the line 14—14 of FIG. 4.
Figure 15:
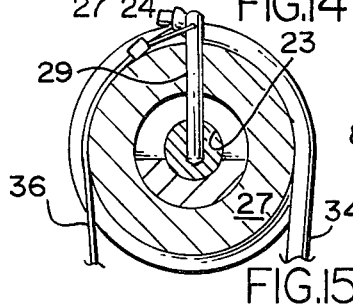
FIG. 15 is a view similar to FIG. 14 with the pulley rotated 90° and is also similar to a cross sectional view taken along the line 15—15 of FIG. 8.
Figure 16:
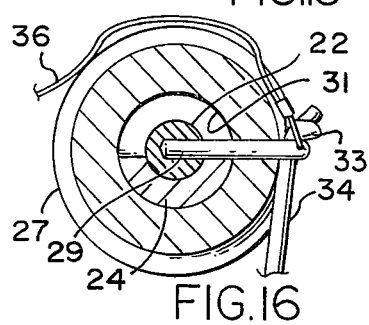
FIG. 16 is a view similar to FIG. 15 with the pulley rotated an additional 90° and is also similar to a cross sectional view taken along the line 16—16 of FIG. 12.
Figure 21:
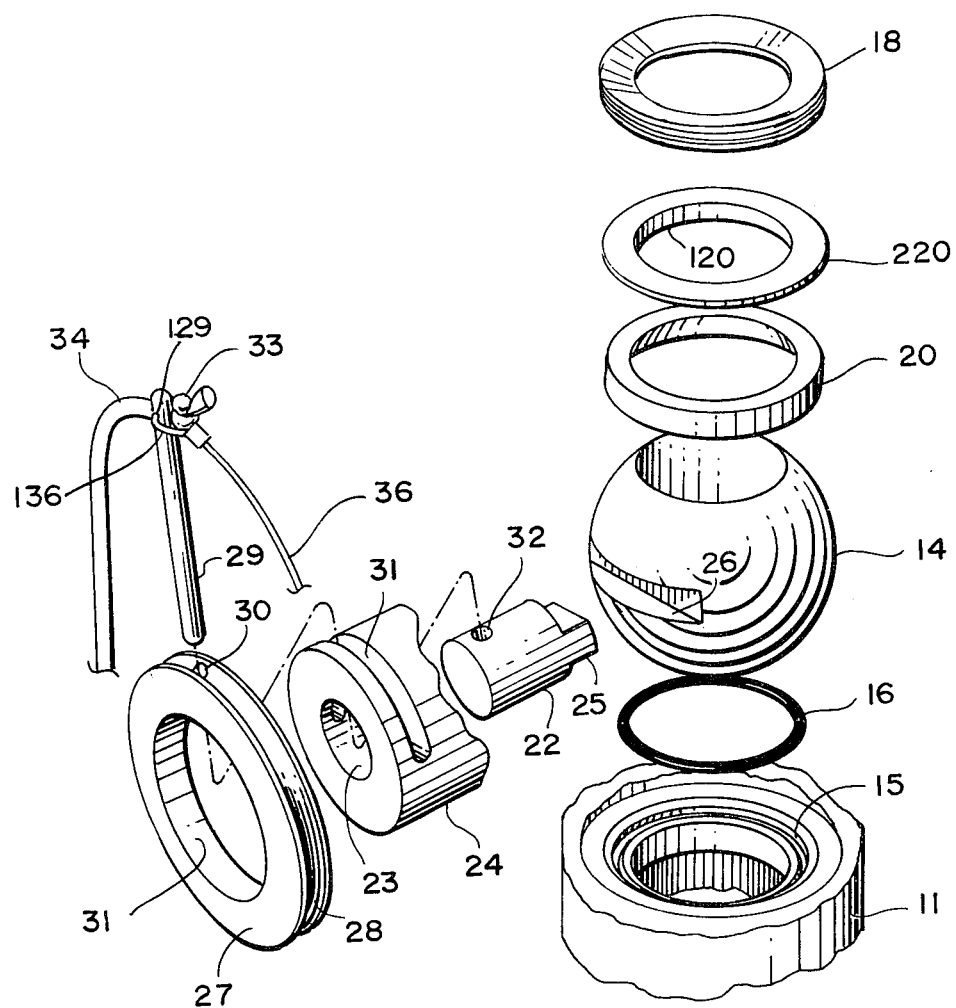
FIG. 21 is an exploded view of the ball valve operating mechanism.

Rotatably mounted on the free end of the boss 24 is a pulley 27 having a peripheral groove 28. See FIGS. 14-16 inclusive. The pulley 27 is retained on the boss 24 by a pin 29 that extends into a radially formed bore 30 in the rim of the pulley 27, through a slot 31 formed in the boss 24 and into a bore 32 formed radially on the valve stem 22 as best shown by FIG. 21. It is to be noted that the slot 31 extends through an arc of 180 degrees about the boss 24, thereby permitting the pulley 27, the valve stem 22 and the ball valve 14 to rotate about an arc of 180°. As will be explained in greater detail hereinafter, the ball valves 14 roate 90° from an initially closed position to an open position, then continue to rotate another 90° to the closed position whereby the ball valves 14 have rotated through a complete arc of 180° in conjunction with the pulleys 27.

The free end of each of the pins 29 is provided with a bore 129 for receiving a loop 136 formed on the end of a lanyard 36 while the end of the elastic band or flexible power cord 34 is knotted as at 33 as shown to prevent the elastic band 34 from being released therefrom. See FIG. 21. The other end of each of the power cords 34 is secured to a T-bracket 35 that is welded or otherwise fastened to the bottle 11. Mounted on the bottle 11 are two pairs of handles 37 symmetrically disposed thereon for readily carrying or otherwise handling the water sampler 10.

Figure 1:
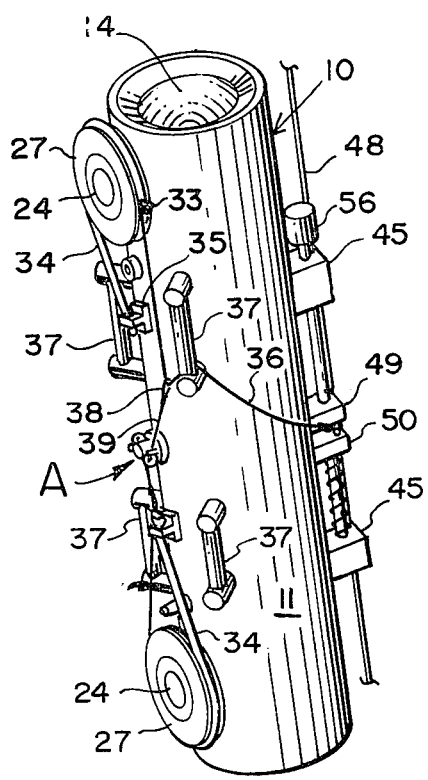
FIG. 1 is a perspective view of a water sampler device constructed in accordance with my invention shown ready for launching.
Figure 23:
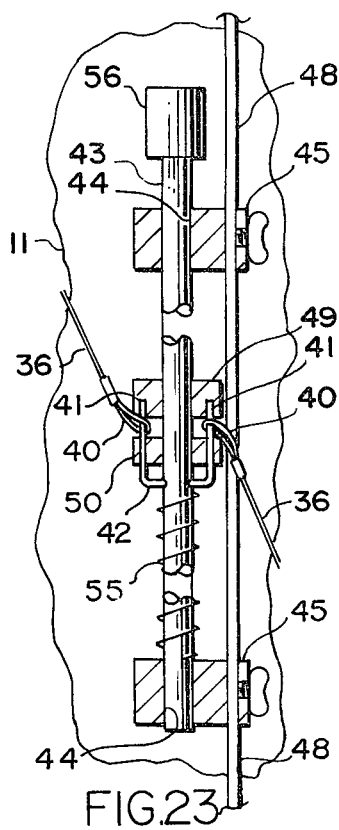
FIG. 23 is a cross sectional view taken along the line 23—23 of FIG. 4.
Figure 24:
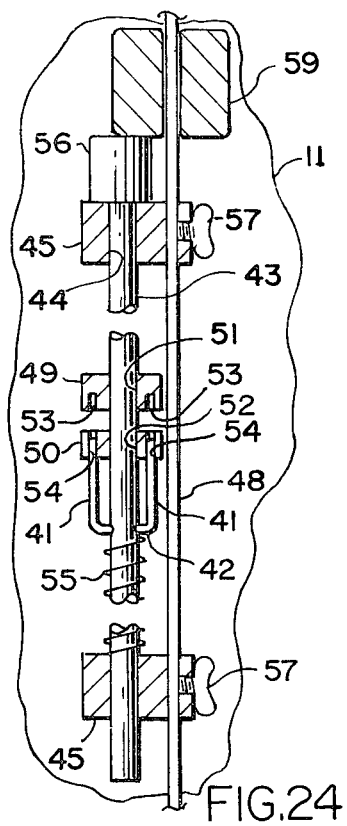
FIG. 24 is a similar view showing the ball valve release mechanism in the released position.

Each of the lanyards 36 extend through a loop 38 formed on the end of a second lanyard 39 and continuing on through one of the handles 37 as shown by FIGS. 1 and 2. The other end of each of the lanyards 36 is provided with a loop 40 that is received on the legs 41 of a U-shaped retaining member 42. The latter is mounted on a shaft 43 that is slidably positioned through bores 44 formed on a pair of spaced brackets 45 secured to the bottle 11 as best shown by FIGS. 23 and 24. An enlarged head portion 56 is mounted on the top end portion of the shaft 43. At approximately the midportion of the slidable shaft 43 is a pair of further brackets 49 and 50 secured to the bottle 11 and having bores 51 and 52 respectively through which the shaft 43 is slidably positioned. The bracket 49 is provided with a pair of blind bores 53 for receiving the end portions of the leg portions 41 of the loop retainer 42 while the bracket 50 is provided with a pair of bores 54 through which their leg portions 41 slidably extend. A coil spring 55 extending between the lower bracket 45 and the loop retainer 42 yieldingly urges the loop retainer 42 into its loop retaining position with the leg portions 41 received in the blind bores 53 as best shown by FIG. 23.

The bottle sampler 10 is suspended on a cable 48 and fastened thereon by winged set screws 57 that secure the cable 48 to the brackets 45. Slidably positioned on the cable 48 is as weighted messenger 59 which is released from an upper position thereon to slide downwardly on the cable 48 to strike the head portion 56 and cause the slide shaft 43 to slide downwardly. This releases the loops 40 of the lanyards 36 for the purpose of effecting a closing of the valves 14 as is explained in detail hereinafter as to the operation of my water sampler device 10.

Figure 17:
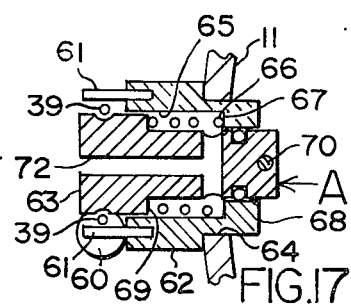
FIG. 17 is a detailed cross sectional view of a combined ball lanyard release and venting valve taken along the line 17—17 of FIG. 2.
Figure 18:
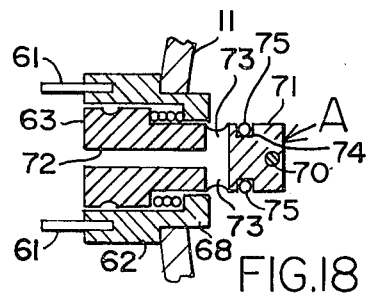
FIG. 18 is a similar view after the valve has been actuated and is also a cross sectional view taken along the line 18—18 of FIG. 6.

The other end of each of the lanyards 39 is connected to an enlarged member or ball 60; the lanyard 39 extending between a pin 61 mounted on a outer valve housing 62 and an inner valve member 63 of a combined water pressure actuated and lanyard retaining and releasing valve -A-. As best shown by FIG. 17, the lanyard balls 60 are held in position on the valve -A- when the inner valve member 63 is in its extended position. When the latter slides inwardly as shown by FIG. 18, the balls 60 and their respective lanyards 39 are released. The valve housing 62 which is mounted on the bottle 11 with an end portion 68 extending through an opening 64 is provided with an open chamber 65 in which the valve member 63 is slidably mounted. A coil spring 66 extends between the end wall 67 of the chamber 65 and a shoulder 69 extending about the valve member 63. The coil spring 66 yieldingly urges the valve member 63 to slide outwardly of the valve housing 62 but its movement is limited by a pin 70 mounted on an end portion 71 of the valve member 63 and engaging the end portion 68 of the valve housing 62. The valve member 63 is provided with an axial bore 72 communicating with radial bores 73. A peripheral slot 74 is formed about the end portion 71 of the valve member 63, in which slot 74 an O-ring 75 is positioned to seal against any leakage at the juncture of the end portions 71 and 68 when the valve member 63 is in its extended position. With the valve member 63 in its extended position, the balls 60 and lanyard 39 are retained in position as shown by FIGS. 1, 2 and 17. The bores 72 and 73 are not in communication with the inner chamber 12 of the bottle 11. When the valve member 63 slides inwardly on the valve housing 62 against the coil spring force 66, the bores 72 and 73 will be in communication with the chamber 12 of the bottle 11 to equalize the higher pressure of the water outside the bottle with the lower pressure of the air in the bottle 11 to permit opening of the ball valves 14 as is explained in detail hereinafter.

Figure 19:
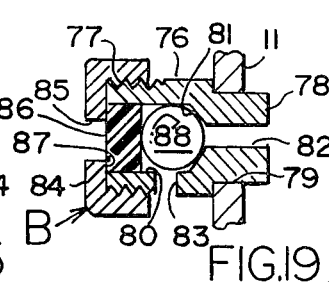
FIG. 19 is a detailed cross sectional view of a combined internal pressure relief valve and air vent taken along the line 19—19 of FIG. 2.
Figure 20:
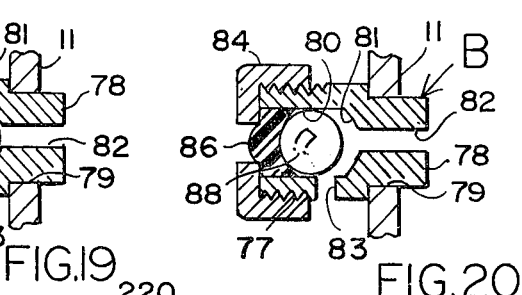
FIG. 20 is a similar view showing the valve when actuated to release internal pressure.

Also mounted on the water bottle 11 is a vent valve -B- for releasing the internal higher pressure of the water during the time when the filled water bottle 11 is being brought to the surface of the body of water as best shown by FIGS. 19 and 20 the vent valve -B- consists of a housing 76 threaded as at 77 and an inner end portion 78 extending through an opening 79 in the bottle 11. The housing 76 is provided with an open chamber 80, having a valve seat 81 connected by a duct 82 along the inner end portion 78 that communicates with the chamber 12 of the bottle 11. A second duct 83 extends radially of the housing 76 to connect the chamber 80 and the areas outside of the bottle 11. A cap 84 threadedly mounted on the valve housing 76 is provided with a centrally disposed opening 85 smaller than that of the chamber 80, thereby forming a peripheral shoulder 87 to engage and retain a flexible diaphragm 86 in position at the end of the chamber 80. Seated on the valve seat 81 and engaging the flexible diaphragm 86 is a ball valve 88 whereby under normal conditions when the pressure on the outside of the bottle 11 is greater than or equal to the pressure inside the bottle 11, the ball valve 88 will remain seated on the valve seat 81 and prevent any flow of fluid from the bottle 11. Upon the pressure within the bottle 11 becoming greater than that outside of the bottle 11, the flexible diaphragm 86 will flex outwardly and the valve 88 becomes unseated as shown by FIG. 20. Water will then flow through the duct 82, chamber 80 and discharge duct 83 until the inside and outside pressures have equalized, at which time the flexible diaphragm 86 will return to its original position and the ball valve 88 will seat itself on the valve seat 81 to cut off any further escape of water therethrough. By removing the cap 84, the relief valve -B- acts as an air vent when emptying the tank 11 of water through a pet cock -C-. See FIGS. 2 and 4.

Figure 22:
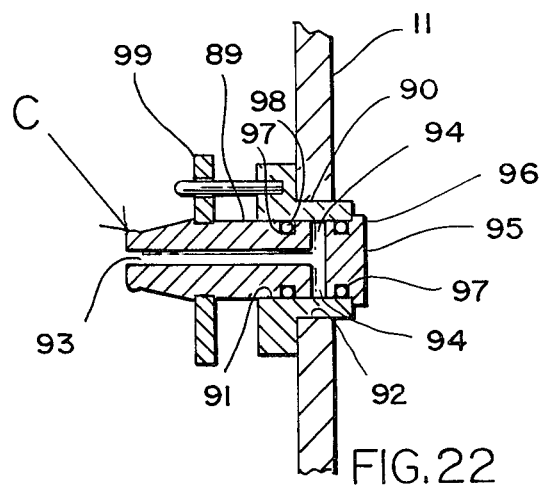
FIG. 22 is a cross sectional view of the stop cock taken along the line 22—22 of FIG. 2.

Mounted on the lower portion of the water sampler bottle 11 is a conventional pet cock -C- consisting of an inner housing 89 slidably mounted in a bore 91 of an outer housing 90 that extends through an opening 92 in the bottle 11. See FIG. 22. The inner housing 89 is provided with an axially disposed duct 93 that extends from the outer end of the housing 89 to lateral ducts 94 positioned in spaced relation to the inner end portion 95. The latter is provided with a peripheral flange 96 to limit the outward sliding movement of the inner housing 89. Peripheral slots 97 are formed about the inner housing 89 on either side of the lateral ducts 94 with O-rings 98 positioned in the slots 97 and engaging the side wall of the bore 91 to prevent leakage of water from the bottle 11 between the inner and outer housings 89 and 90. A handle 99 mounted on the inner housing 89 permits sliding the inner housing 89 inwardly to position the lateral openings 94 beyond the outer housing 90 so that water contained in the bottle 11 can now be drawn therefrom through the ducts 94 and 93. The pet cock -C- as shown by FIG. 22 is in its closed position.

Figure 8:
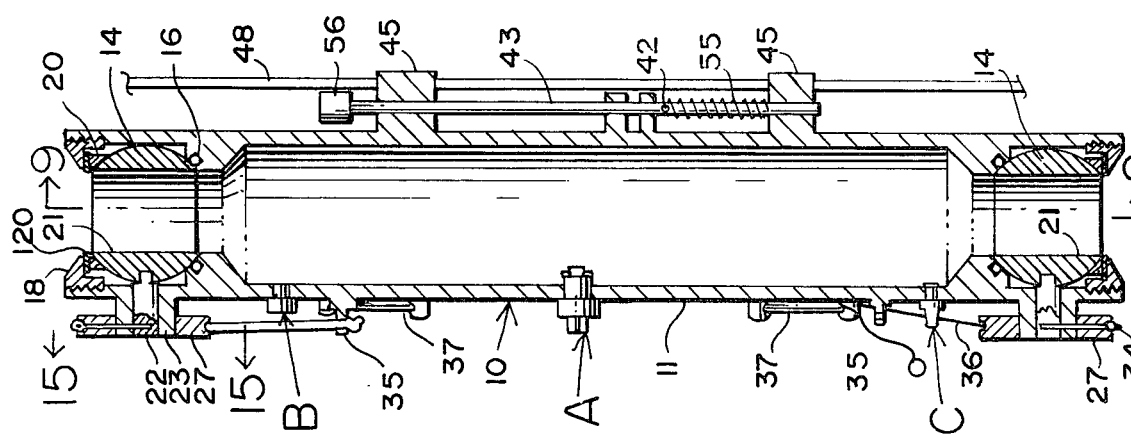
FIG. 8 is a cross sectional view taken along the line 8—8 of FIG. 6.
Figure 7:
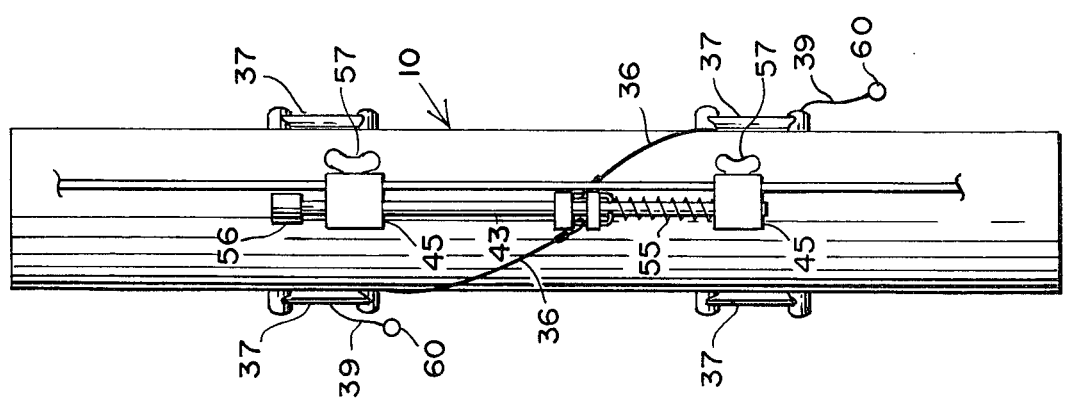
FIG. 7 is a similar view showing the obverse side.
Figure 6:
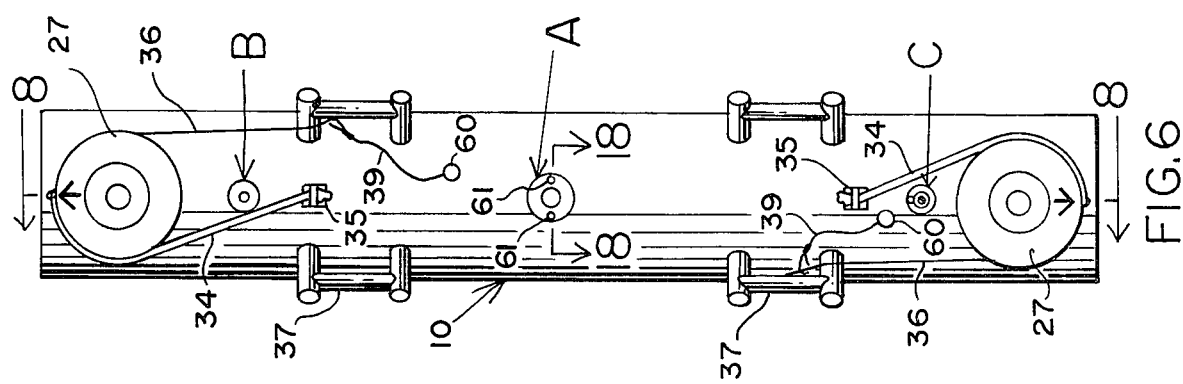
FIG. 6 is a view similar to FIG. 2 after launching with the ball valves in an open position to permit water to flow through the water sampler bottle.
Figure 11:
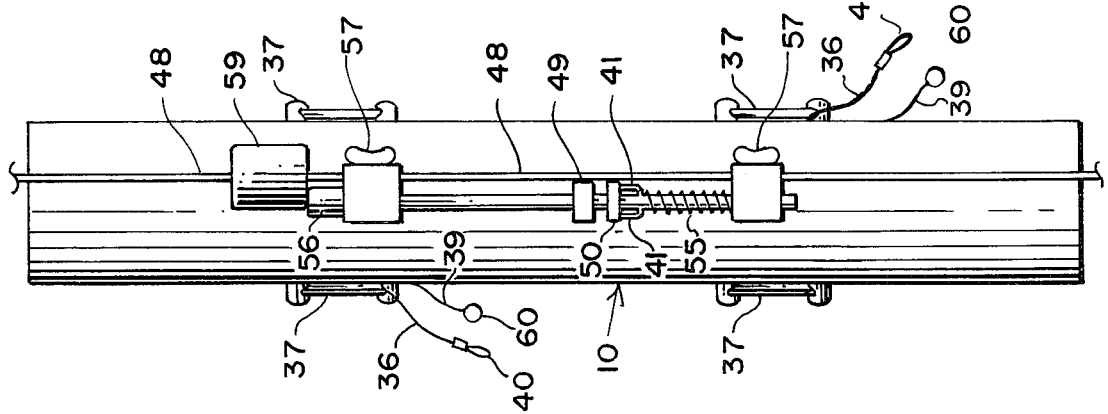
FIG. 11 is a similar view showing the obverse side.
Figure 13:
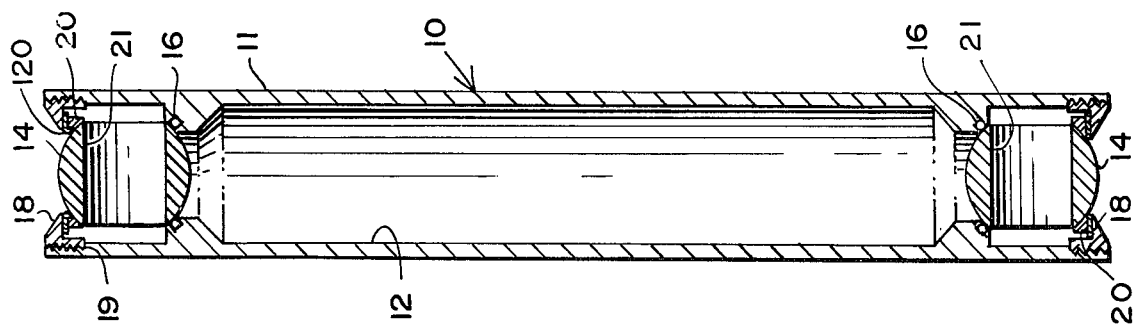
FIG. 13 is a cross sectional view taken along the line 13—13 of FIG. 12.
Figure 10:
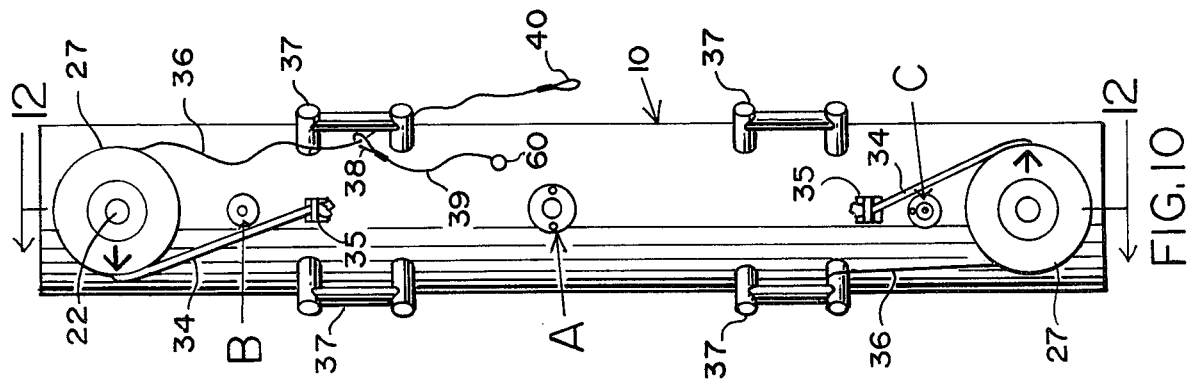
FIG. 10 is a view similar to FIGS. 2 and 6 with the ball valves in a closed position after the bottle has been filled with a water sample.

In the normal use of my water sampler device 10 for obtaining a sample of water at a predetermined depth of ocean water, the bottle 11 will have been evacuated of water, sterilized to remove any contaminants therein and stored in the condition as shown by FIGS. 10-13 inclusive. The water sampler device 10 will be secured to the cable 48 at the brackets 45 as shown by FIG. 11; at this position of the cable 48 which when lowered over the side into the ocean will place the bottle 10 at the desired depth; at which time the messenger 59 will be released to actuate the mechanism for containing the sample of water in the bottle 11 as is explained hereinafter. With the water sampler bottle 10 as shown by FIG. 10, the lanyards 36 are grasped and pulled until the pulleys 27 are rotated through an arc of 90° against the force of the power cords 34 to rotate the ball valves 14 to their open position. The loops 40 of the lanyards 36 are slipped over the legs 41 of the retainer 42 after the slide shaft 43 has been depressed to the position shown by FIG. 24 and then released to the position shown by FIG. 23. The sampler device 10 now has its various parts in the position as shown by FIGS. 6-8 inclusive. Lanyards 39 with their loops 38 slidably positioned on the lanyards 36 which are in the position shown by FIG. 6 are now grasped and pulled forcibily to cause the lanyards 36 to apply a second pulling force in the power cords or elastic bands 34 whereby the pulleys 27 are rotated through a further arc of 90° to cause the valves 14 to rotate to their closed positions. The ends of the lanyards 39 are positioned between valve member 63 and retaining pins 61 whereby the balls 60 become engaged against movement therebetween. See FIG. 17. Now the various parts of the water sampler 10 are in the positions as shown by FIGS. 2-5 inclusive. The valves 14 are now in their closed position, and the water sampler device 10 is ready for launching to obtain a sample of water. At this time, the pet cock -C- will be in its closed position and the valve 88 of the pressure relief valve -B- will be seated as shown by FIG. 19.

Now when the water sampler device 10 is lowered into the water the contaminants floating on the surface and just below the surface of the water cannot enter into the bottle 11 since the ball vaves 14 are in a closed position. After the bottle 11 has been lowered a relatively short distance, the water pressure will force the valve -A- to its open position as shown by FIG. 18 to simultaneously permit water to flow through the ducts 72, 73 and into the bottle 11 and to release the lanyard balls 60 and lanyards 39. The pressures outside and inside the bottle 11 are now equalized to permit the easy rotation of the ball valves 14 through an arc of 90° to the open position. This was accomplished upon the lanyards 36 being partially released to permit the power cords 34 to rotate the pulleys 27 which in turn rotated the ball valves 14 to the open position. The force of the power cords 34 cause the lanyards 36 to become taut as their loops 40 are still engaged by the retainer pins 41 as shown by FIG. 23.

Figure 9:
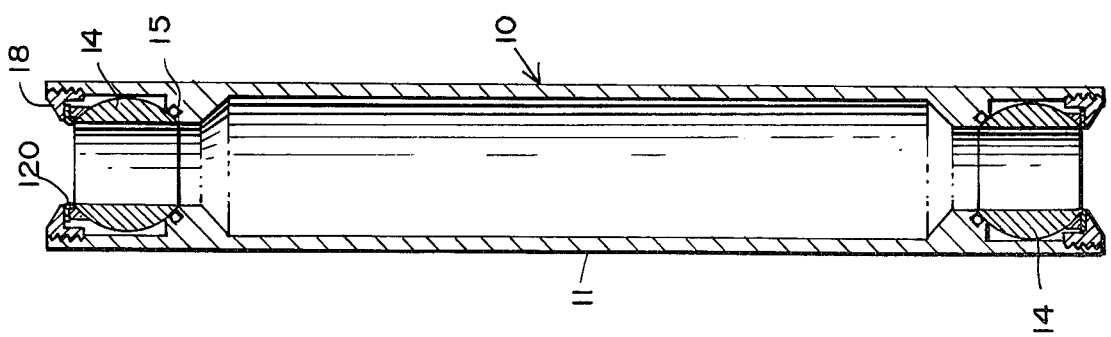
FIG. 9 is a similar view taken along the line 9—9 of FIG. 8.

The continued lowering of water sampler device 11, with its ball valves 14 in their open position permits the water to flow through the entire length of the bottle 11 to flush same continually during the lowering process. See FIGS. 8 and 9.

When the sampler device 10 has arrived at the predetermined depth at which a sample of water is desired, the messenger 59 is slid down the cable 48 and made to strike the head 56 of the slide shaft 43. The latter will slide downwardly of their brackets 45 carrying the retainer pins 41 downwardly of the brackets 51, 50 to release the loops 40 of the lanyards 36. The power cords 34 are now able to effect the rotation of the pulleys 27 and their respective ball valves 14 through a second arc of 90° to bring the latter to the closed positions as shown by FIGS. 10-13 inclusive.

The bottle 11 of the sampler device 10 now filled with the desired sample of water is now brought up to the surface of the ocean. As the pressure of the ocean water on the sampler 10 lessens while the latter is ascending, the higher water pressure trapped within the bottle 11 will cause the pressure relief valve -B- move to its open position to release some water as shown by FIG. 20 thereby cause the pressures inside and outside the sampler 10 to become equalized.

After the sampler device 10 has been brought on deck, if a boat was used to launch same, the water contained in the bottle 11 is evacuated through the conventional pet cock -C-. At the same time, the cap 84 of the pressure relief valve -B- is removed from the valve housing 76 to permit air to enter into the bottle 11 as the water is pouring out through the pet cock -C-.

It is to be noted that my water sampler device 10 as described hereinabove in connection with the drawings may be utilized individually to obtain a single water sample or in groups as shown and described in my U.S. Pat. Nos. 3,242,740 and 3,489,012, whereby a number of samples of water may be obtained simultaneously at various predetermined depths in the ocean. The bottles 11 will contain uncontaminated samples of water taken from desired depths in the ocean quickly and with a minimal of effort. The water sampler devices 10 are capable of being used as often as desired by merely cleansing the inside of the bottles 11 after evacuating the sample of water and resetting the various mechanisms as described hereinabove prior to each launching.

What I claim as new and desire to secure by Letters Patent is:

1. A water sampler device for collecting a sample of water at a desired depth in a body of water comprising a substantially elongated tubular member, valve seat means mounted at each end of said tubular member, substantially spherical valve means mounted on each of said valve seat means in an initially closed position to prevent contaminated surface waters of said body of water from entering into said tubular members, valve rotating means connected to each of said valve means, valve operating means connected to said valve rotating means for consecutively rotating each of said valve means from said closed position to an open position to permit the flow of fluid through said tubular member when said device has arrived at said depth in said body of water and then to a further closed position to contain water in said tubular member.

2. The structure as recited by claim 1 wherein said valve means rotates through an arc of substantially 180° and valve restraining means operatively connected to said valve operating means preventing said valve rotating means from rotating said valve means from said open to said closed position until said device has arrived at said depth in said body of water.

3. The structure as recited by claim 2 wherein said valve operating means comprises hydrostatically operated means mounted on said tubular member and pliable means connecting said hydrostatically operated means and said valve rotating means whereby upon the actuation of said hydrostatically operated means said pliable means effects the actuation of said valve rotating means to rotate said valve means for said initially closed position to an open position.

4. The structure as recited by claim 3 wherein said hydrostatically operated means comprises a housing, said tubular member having an opening receiving said housing, said housing having a chamber, a valve body having an outer portion and inner portion and being slidably mounted in said chamber with said inner portion extending into said tubular member, spring means yieldingly urging said valve body in an outward direction away from said tubular member, means limiting the outward movement of said valve body, duct means extending from said outer portion to a position adjacent to said inner portion whereby upon the sliding movement of said valve body in the inward direction said duct means will communicate with said tubular member and upon the equalization of pressures within and without said tubular member, said spring means will effect the outward sliding movement of said valve body with said duct means not communicating with said tubular member.

5. The structure as recited by claim 4 wherein said valve means comprises spherical body member having an opening extending through said body member and said valve seat means comprises a peripheral shoulder extending about the inner portion of said tubular member, pliable seal means mounted on said shoulder and engaged by said spherical body member, said opening being substantially smaller in diameter than that of said peripheral shoulder.

6. The structure as recited by claim 5 wherein said valve rotating means comprises a hub portion mounted on said tubular member, said hub portion having a peripheral groove extending substantially partially about the circumference of said hub portion, said hub portion having a bore, a valve stem extending through said and bore and engaging said spherical body member, a pulley rotatably mounted on said hub portion, said pulley having a radially disposed opening, a pin extending through said opening in said pulley and through said peripheral groove in said hub portion and secured at one end to said valve stem with its other end being connected to said pliable means.

7. The structure as recited by claim 6 having an elongated flexible member wound about said pulley and connected at one end to said tubular member and its other end to one end of said lanyard means for yieldingly urging the rotation of said pulley with the other end of said lanyard means being connected to said restraining means.

8. The structure as recited by claim 7 wherein said restraining means comprises a shaft slidably mounted on said tubular member, means mounted on said shaft releasably retaining said other end of said lanyard means, yielding means urging said shaft in a direction for retaining said lanyard means, means for sliding said shaft against said yielding means for releasing said lanyard means.

9. The structure as recited by claim 8 wherein said restraining means further comprises a second lanyard means having one end releasably connected to said hydrostatically operated means, and the other end having a loop portion engaging said first named lanyard intermediate its end whereby upon actuation of said hydrostatically operated means said second lanyard means releases said first named lanyard means to effect a partial rotation of said pulley whereby said ball valve will rotate from a closed to an open position and upon the sliding of said shaft against said yielding means said first named lanyard means is released to effect a further rotation of said ball valve to a closed position to retain fluid contained in said tubular member.

10. A water sampler device comprising an elongated tubular member, a peripheral shoulder extending about the inner portion of said tubular member adjacent to one end thereof and forming a valve seat, a substantially spherical valve rotatably mounted on said valve seat selectively from closed, to open and then to a closed position, seal means mounted on said valve seat and engaging said spherical valve, said valve having a substantially radially disposed opening for the flow of fluid therethrough, means selectively rotating said spherical valve to allow fluid to flow into said tubular member at a preselected depth, pliable valve seat ring means positioned on said spherical valve about said opening when said spherical valve is in an open position, floating valve seat retainer ring positioned on said pliable valve seat ring means, said floating valve seat retainer ring means having a peripheral lip portion engaging said pliable valve seat ring means and a lock ring removably secured to the free end of said elongated tubular member and engaging said valve seat retainer ring means.

11. The structure as recited by claim 10 wherein said seal means comprises an O-ring and said lip portion extends about the inner periphery of said floating valve seat ring preventing the distortion of said pliable valve seat ring means upon the rotation of said spherical valve and compels said spherical valve to remain in alignment with said O-ring.

* * * * *